US009301787B2

(12) United States Patent
Malek (10) Patent No.: US 9,301,787 B2
(45) Date of Patent: Apr. 5, 2016

(54) MEDICAL APPARATUS AND METHOD FOR SPINAL SURGERY

(75) Inventor: Michel H. Malek, Chicago, IL (US)

(73) Assignee: MMSN Limited Partnership, Kankakee, IL (US)

( * ) Notice: Subject to any disclaimer, the term of this patent is extended or adjusted under 35 U.S.C. 154(b) by 175 days.

(21) Appl. No.: 12/891,557

(22) Filed: Sep. 27, 2010

(65) Prior Publication Data

US 2012/0078303 A1  Mar. 29, 2012

(51) Int. Cl.
*A61B 17/70* (2006.01)

(52) U.S. Cl.
CPC ......... *A61B 17/7067* (2013.01); *A61B 17/7049* (2013.01); *A61B 17/7052* (2013.01)

(58) Field of Classification Search
USPC ................................. 606/246–250, 251–278
See application file for complete search history.

(56) References Cited

U.S. PATENT DOCUMENTS

| 4,011,602 | A | 3/1977 | Rybicki et al. |
| 4,349,921 | A | 9/1982 | Kuntz |
| 4,401,112 | A | 8/1983 | Resaian |
| 4,643,178 | A | 2/1987 | Nastari et al. |
| 4,657,550 | A | 4/1987 | Daher |
| 4,743,256 | A | 5/1988 | Brantigan |
| 4,743,260 | A | 5/1988 | Burton |
| 4,759,766 | A | 7/1988 | Büettner-Janz et al. |
| 4,759,769 | A | 7/1988 | Hedman et al. |
| 4,863,476 | A | 9/1989 | Shepperd |
| 4,946,378 | A | 8/1990 | Hirayama et al. |
| 4,946,458 | A | 8/1990 | Harms et al. |
| 4,997,432 | A | 3/1991 | Keller |
| 5,024,670 | A | 6/1991 | Smith et al. |
| 5,084,048 | A | 1/1992 | Jacob et al. |
| 5,092,866 | A | 3/1992 | Breard et al. |
| 5,122,130 | A | 6/1992 | Keller |
| 5,246,458 | A | 9/1993 | Graham |
| 5,258,031 | A | 11/1993 | Salib et al. |
| 5,261,911 | A | 11/1993 | Carl |
| 5,275,600 | A | * 1/1994 | Allard et al. .................. 606/252 |
| 5,282,863 | A | 2/1994 | Burton |

(Continued)

FOREIGN PATENT DOCUMENTS

| DE | 30 23 353 A1 | 4/1981 |
| EP | 0 176 728 A | 4/1986 |
| EP | 0 560 140 B1 | 9/1993 |
| EP | 0 560 141 A | 9/1993 |
| EP | 0 566 810 B1 | 10/1993 |
| FR | 2 694 882 A | 2/1994 |
| FR | 2 801 782 | 6/2001 |
| FR | 2 805 985 | 9/2001 |
| WO | WO 94/04100 | 3/1994 |
| WO | WO 95/26697 | 10/1995 |
| WO | WO 01/06939 | 2/2001 |
| WO | WO 02/24087 | 3/2002 |
| WO | WO 03/094699 | 11/2003 |
| WO | WO 2008/014337 | 1/2008 |
| WO | WO 2009/088746 | 7/2009 |
| WO | WO 2009/100117 | 8/2009 |

OTHER PUBLICATIONS

European Patent Office Search Report for Application No. 04812086.9, dated Aug. 19, 2011, 5 pages.
The International Search Report and Written Opinion for PCT/US2004/032116 mailed on Feb. 16, 2005, 12 pages.
"Anatomic Facet Replacement System (AFRS™)," *Natural Motion*; published by Facet Solutions, Inc.; http://www.facetsolutions.com/Device.html on or before Nov. 2, 2007, 1 page.

*Primary Examiner* — Jan Christopher Merene
(74) *Attorney, Agent, or Firm* — Foley & Lardner LLP (57) ABSTRACT

A medical apparatus for use proximate a surgery location on a spine of a subject includes a first lateral support member and a second lateral support member, each lateral support member coupled to a portion of the spine proximate a first vertebra. A transverse connection member has a first end, a second end, and an intermediate portion therebetween, with the first end coupled to the first lateral support member and the second end coupled to the second lateral support member. A first extension member has a first end and a second end, with the first end coupled to the intermediate portion of the transverse connection member, and the second end coupled to a spinous process of a second vertebra.

12 Claims, 6 Drawing Sheets

(56) References Cited

U.S. PATENT DOCUMENTS

| | | |
|---|---|---|
| 5,306,310 A | 4/1994 | Siebels |
| 5,314,477 A | 5/1994 | Marnay |
| 5,314,478 A | 5/1994 | Oka et al. |
| 5,336,223 A | 8/1994 | Rogers |
| 5,352,224 A | 10/1994 | Westermann |
| 5,375,823 A | 12/1994 | Navas |
| 5,380,324 A | 1/1995 | Müller et al. |
| 5,380,328 A | 1/1995 | Morgan |
| 5,401,269 A | 3/1995 | Buttner-Janz et al. |
| 5,415,659 A | 5/1995 | Lee et al. |
| 5,437,671 A | 8/1995 | Lozier et al. |
| 5,458,641 A | 10/1995 | Ramirez Jimenez |
| 5,487,742 A * | 1/1996 | Cotrel .......................... 606/252 |
| 5,496,318 A | 3/1996 | Howland et al. |
| 5,534,029 A | 7/1996 | Shima |
| 5,536,124 A | 7/1996 | Silva |
| 5,540,688 A | 7/1996 | Navas |
| 5,556,431 A | 9/1996 | Buttner-Janz |
| 5,562,738 A | 10/1996 | Boyd et al. |
| 5,591,166 A | 1/1997 | Bernhardt et al. |
| 5,607,425 A | 3/1997 | Rogozinski |
| 5,628,740 A | 5/1997 | Mullane |
| 5,645,596 A | 7/1997 | Kim et al. |
| 5,649,925 A | 7/1997 | Barbera Alacreu |
| 5,672,175 A | 9/1997 | Martin |
| 5,688,275 A | 11/1997 | Koros et al. |
| 5,702,453 A | 12/1997 | Rabbe et al. |
| 5,702,455 A | 12/1997 | Saggar |
| 5,713,899 A | 2/1998 | Marnay et al. |
| 5,725,582 A | 3/1998 | Bevan et al. |
| 5,776,198 A | 7/1998 | Rabbe et al. |
| 5,836,948 A | 11/1998 | Zucherman et al. |
| 5,888,226 A | 3/1999 | Rogozinski |
| 5,893,889 A | 4/1999 | Harrington |
| 5,951,553 A | 9/1999 | Betz et al. |
| 5,989,290 A | 11/1999 | Biedermann et al. |
| 6,019,792 A | 2/2000 | Cauthen |
| 6,030,389 A | 2/2000 | Wagner et al. |
| 6,063,121 A | 5/2000 | Xavier et al. |
| 6,074,390 A | 6/2000 | Zucherman et al. |
| 6,083,224 A | 7/2000 | Gertzbein et al. |
| 6,113,637 A | 9/2000 | Gill et al. |
| 6,136,000 A * | 10/2000 | Louis et al. ................... 606/250 |
| 6,139,579 A | 10/2000 | Steffee et al. |
| 6,146,421 A | 11/2000 | Gordon et al. |
| 6,179,874 B1 | 1/2001 | Cauthen |
| 6,214,012 B1 | 4/2001 | Karpman et al. |
| 6,217,578 B1 | 4/2001 | Crozet et al. |
| 6,228,118 B1 | 5/2001 | Gordon |
| 6,241,730 B1 | 6/2001 | Alby |
| 6,293,949 B1 | 9/2001 | Justis et al. |
| 6,296,644 B1 | 10/2001 | Saurat et al. |
| 6,296,664 B1 | 10/2001 | Middleton |
| 6,315,797 B1 | 11/2001 | Middleton |
| 6,368,350 B1 | 4/2002 | Erickson et al. |
| 6,375,682 B1 | 4/2002 | Fleischmann et al. |
| 6,375,683 B1 | 4/2002 | Crozet et al. |
| 6,395,034 B1 | 5/2002 | Suddaby |
| 6,402,750 B1 | 6/2002 | Atkinson et al. |
| 6,419,703 B1 | 7/2002 | Fallin et al. |
| 6,454,807 B1 | 9/2002 | Jackson |
| 6,478,800 B1 | 11/2002 | Fraser et al. |
| 6,500,178 B2 | 12/2002 | Zucherman et al. |
| 6,517,580 B1 | 2/2003 | Ramadan et al. |
| 6,520,990 B1 | 2/2003 | Ray |
| 6,540,785 B1 | 4/2003 | Gill et al. |
| 6,554,831 B1 | 4/2003 | Rivard et al. |
| 6,565,605 B2 | 5/2003 | Goble et al. |
| 6,579,319 B2 | 6/2003 | Goble et al. |
| 6,579,320 B1 | 6/2003 | Gauchet et al. |
| 6,582,466 B1 | 6/2003 | Gauchet |
| 6,582,468 B1 | 6/2003 | Gauchet |
| 6,585,769 B1 | 7/2003 | Muhanna et al. |
| 6,607,558 B2 | 8/2003 | Kuras |
| 6,616,669 B2 | 9/2003 | Ogilvie et al. |
| 6,626,905 B1 | 9/2003 | Schmiel et al. |
| 6,626,908 B2 | 9/2003 | Cooper et al. |
| 6,652,585 B2 | 11/2003 | Lange |
| 6,685,742 B1 | 2/2004 | Jackson |
| 6,695,842 B2 | 2/2004 | Zucherman et al. |
| 6,730,126 B2 | 5/2004 | Boehm et al. |
| 6,752,831 B2 | 6/2004 | Sybert et al. |
| 6,761,720 B1 | 7/2004 | Senegas |
| 6,764,515 B2 | 7/2004 | Ralph et al. |
| 6,835,205 B2 | 12/2004 | Atkinson et al. |
| 6,852,128 B2 | 2/2005 | Lange |
| 6,902,566 B2 | 6/2005 | Zucherman et al. |
| 6,946,000 B2 | 9/2005 | Senegas et al. |
| 6,966,910 B2 | 11/2005 | Ritland |
| 6,966,931 B2 | 11/2005 | Huang |
| 6,989,011 B2 | 1/2006 | Paul et al. |
| 7,022,138 B2 | 4/2006 | Mashburn |
| 7,025,787 B2 | 4/2006 | Bryan et al. |
| 7,041,138 B2 | 5/2006 | Lange |
| 7,044,970 B2 | 5/2006 | Errico et al. |
| 7,056,343 B2 | 6/2006 | Schafer et al. |
| 7,101,375 B2 | 9/2006 | Zucherman et al. |
| 7,147,665 B1 | 12/2006 | Bryan et al. |
| 7,175,623 B2 | 2/2007 | Thramaan et al. |
| 7,186,256 B2 | 3/2007 | Michelson |
| 7,201,751 B2 | 4/2007 | Zucherman et al. |
| 7,255,713 B2 | 8/2007 | Malek |
| 7,282,064 B2 | 10/2007 | Chin |
| 7,318,825 B2 | 1/2008 | Butler et al. |
| 7,402,176 B2 | 7/2008 | Malek |
| 7,524,324 B2 * | 4/2009 | Winslow et al. ............... 606/248 |
| 8,048,120 B1 * | 11/2011 | Fallin et al. .................... 606/249 |
| 2001/0016773 A1 | 8/2001 | Serhan et al. |
| 2001/0029375 A1 | 10/2001 | Betz et al. |
| 2001/0032020 A1 | 10/2001 | Besselink |
| 2001/0037111 A1 | 11/2001 | Dixon et al. |
| 2001/0051829 A1 | 12/2001 | Middleton |
| 2002/0022888 A1 | 2/2002 | Serhan et al. |
| 2002/0107574 A1 | 8/2002 | Boehm et al. |
| 2002/0111683 A1 | 8/2002 | Ralph et al. |
| 2002/0147454 A1 | 10/2002 | Neto |
| 2003/0009223 A1 | 1/2003 | Fehling et al. |
| 2003/0009226 A1 | 1/2003 | Graf |
| 2003/0018390 A1 | 1/2003 | Husson |
| 2003/0023312 A1 | 1/2003 | Thalgott |
| 2003/0032958 A1 | 2/2003 | Soubeiran |
| 2003/0055427 A1 | 3/2003 | Graf |
| 2003/0100951 A1 | 5/2003 | Serhan et al. |
| 2003/0176861 A1 | 9/2003 | Reed |
| 2003/0191534 A1 | 10/2003 | Viart et al. |
| 2003/0229348 A1 | 12/2003 | Sevrain |
| 2004/0002762 A1 | 1/2004 | Hawkins |
| 2004/0153156 A1 | 8/2004 | Cohen et al. |
| 2004/0167626 A1 | 8/2004 | Geremakis et al. |
| 2005/0085910 A1 | 4/2005 | Sweeney |
| 2005/0113927 A1 | 5/2005 | Malek |
| 2005/0143823 A1 | 6/2005 | Boyd et al. |
| 2005/0165486 A1 | 7/2005 | Trieu |
| 2005/0203518 A1 * | 9/2005 | Biedermann et al. ........... 606/61 |
| 2005/0209593 A1 | 9/2005 | Kolb |
| 2005/0209697 A1 | 9/2005 | Paponneau et al. |
| 2005/0234425 A1 | 10/2005 | Miller et al. |
| 2006/0036243 A1 | 2/2006 | Sasso et al. |
| 2006/0058791 A1 * | 3/2006 | Broman et al. ................. 606/61 |
| 2006/0064090 A1 * | 3/2006 | Park ............................... 606/61 |
| 2006/0079895 A1 | 4/2006 | McLeer |
| 2006/0106381 A1 | 5/2006 | Ferree et al. |
| 2006/0161154 A1 | 7/2006 | McAfee |
| 2006/0200140 A1 | 9/2006 | Lange |
| 2006/0224223 A1 | 10/2006 | Podhajsky et al. |
| 2006/0241601 A1 * | 10/2006 | Trautwein .......... A61B 17/7049<br>606/248 |
| 2006/0293662 A1 * | 12/2006 | Boyer et al. .................... 606/61 |
| 2007/0010813 A1 | 1/2007 | Zucherman et al. |
| 2007/0112299 A1 | 5/2007 | Smit et al. |
| 2007/0161993 A1 * | 7/2007 | Lowery et al. .................. 606/61 |
| 2007/0173937 A1 | 7/2007 | Khalili |
| 2007/0270828 A1 | 11/2007 | Bruneau et al. |
| 2008/0027444 A1 | 1/2008 | Malek |

(56) References Cited

U.S. PATENT DOCUMENTS

| | | | |
|---|---|---|---|
| 2008/0177318 A1* | 7/2008 | Veldman et al. | 606/256 |
| 2008/0177326 A1* | 7/2008 | Thompson | 606/277 |
| 2009/0062919 A1 | 3/2009 | Malek | |
| 2009/0149885 A1* | 6/2009 | Durward et al. | 606/246 |
| 2009/0177233 A1 | 7/2009 | Malek | |
| 2009/0204149 A1 | 8/2009 | Malek | |
| 2009/0287118 A1 | 11/2009 | Malek | |
| 2009/0318968 A1* | 12/2009 | Duggal et al. | 606/250 |
| 2010/0049252 A1* | 2/2010 | Smisson et al. | 606/250 |
| 2010/0094345 A1* | 4/2010 | Saidha et al. | 606/250 |
| 2010/0106193 A1* | 4/2010 | Barry | 606/264 |
| 2010/0121378 A1 | 5/2010 | Malek | |
| 2010/0160964 A1 | 6/2010 | Malek | |
| 2010/0222818 A1* | 9/2010 | Trieu et al. | 606/254 |
| 2012/0109202 A1* | 5/2012 | Kretzer | A61B 17/7049 606/248 |
| 2014/0309694 A1* | 10/2014 | Kretzer | A61B 17/7049 606/248 |

* cited by examiner

Step 502: implanting a first lateral support member and a second lateral support member proximate the spinal surgery location.

↓

Step 504: implanting a transverse connection member having a first end, a second end, and an intermediate portion there between, and coupling the first end to the first lateral support member and the second end to the second lateral support member.

↓

Step 506: implanting a first extension member having a first end and a second end, and coupling the first end to the intermediate portion of the transverse connection member, and coupling the second end to a spinous process of a second vertebra.

↓

Step 508: implanting a second extension member having a first end and a second end, and coupling the first end to the intermediate portion of the transverse connection member, and coupling the second end to a spinous process of a third vertebra.

↓

Step 510: implanting a second extension member having a first end and a second end, and coupling the first end to the spinous process of the second vertebra, and coupling the second end to a spinous process of a third vertebra.

↓

Step 512: implanting a second extension member having a first end and a second end, and coupling the first end to the intermediate portion of the transverse connection member, and coupling the second end to the spinous process of the second vertebra in a bilateral arrangement with the first extension member.

FIGURE 6

MEDICAL APPARATUS AND METHOD FOR SPINAL SURGERY

FIELD

The invention generally relates to medical apparatuses for the spine. More specifically, medical systems, apparatuses and methods are disclosed which are capable of transferring flexion or bending motion along the spine to one or more vertebrae above and/or below a spinal surgery location (e.g. vertebral fusion, laminotomy, laminectomy, diskectomy, etc.) thereby alleviating, mitigating or preventing excessive wear and tear or other flexion-related degradation of spinal elements that are directly adjacent to the spinal surgery location.

BACKGROUND

Spinal surgery may include any one or more of a number of procedures. For example, a laminotomy is a surgical technique that removes a portion o the lamina (i.e. the bone at the back of the spinal canal). The small opening that is created is sometimes enough to relieve pressure from a nerve, but in some cases, part of an intervertebral disk or a bone spur that is pressing on the nerve may also be removed. Also by way of example, a laminectomy is a surgical technique that generally removes the entire lamina to relieve pressure when a disk bulges into a nerve. Further, a diskectomy is a surgical technique that removes a portion of a damaged disk from between adjacent vertebrae to relieve pressure on the nerve. Also, vertebral fusion is a surgical technique used to combine two or more vertebrae. Supplementary bone tissue (either autograft or allograft) is typically used in conjunction with the body's natural osteoblastic processes. This procedure is often used to eliminate pain caused by abnormal motion of the vertebrae by immobilizing the vertebrae themselves. Spinal fusion is done most commonly in the lumbar region of the spine, but it is also used to treat cervical and thoracic problems. There are generally two main types of lumbar spinal fusion, which may be used in conjunction with each other. Posterolateral fusion places the bone graft between the transverse processes in the back of the spine. These vertebrae are then fixed in place with screws and/or wire through the pedicles of each vertebra attaching to a metal rod on each side of the vertebrae. Interbody fusion places the bone graft between the vertebra in the area usually occupied by the intervertebral disc. The fusion then occurs between the endplates of the vertebrae.

However, such known spinal fusion techniques tend to have certain disadvantages. For example, the vertebrae that have been fused and immobilized together are no longer able to flex relative to one another to assist in the flexing the spine through a normal range of motion. Also, due to the immobility of the fused vertebrae, the spinal elements (e.g. intervertebral discs, vertebrae, etc.) that are adjacent to the fused vertebrae tend to be subject to increased flexion demands (and associated wear and tear and other related degradation) as the spine seeks to accommodate a normal range of motion. A simplified example of such a phenomenon may be seen in a flexible tube have and immobilized (i.e. rigidified) segment, whereupon bending or flexing of the entire tube tends to result in increased stress, or even damage (e.g. kinking, etc.) of the tube at the locations directly adjacent to the rigid segment. Also, other spinal surgery techniques may also tend to result in reduced capability of the remaining spinal elements to accommodate the normal range of spinal motion, or may result in undesirable (e.g. non-uniform) distribution of loading across the spinal elements. It is also generally known to provide a prosthetic spinous process, such as those described in U.S. Patent Application Publication No. US 2006/0161154 A1 titled "Prosthetic Spinous Process and Method" for use in surgical applications where the spinous process is removed or otherwise missing. However, such prosthetic spinous process devices are of limited utility or applicability in spinal surgical techniques where the spinous process remains intact following the surgery.

Accordingly, it would be desirable to provide a universal medical apparatus and method for spinal surgery that helps to overcome the disadvantages of a variety of know spinal surgical techniques and devices. It would also be desirable to provide a medical apparatus and method for spinal surgery that transfers loads (e.g. flexion loads, bending loads, etc.) and other related stresses from the locations directly adjacent to the surgery location (e.g. fused vertebrae, etc.) to other vertebrae above and/or below the surgery location by interconnecting the spinous processes of the adjacent vertebrae in a load-sharing manner, so that bending loads and other stresses may be spread over (and at least partially accommodated by) such other vertebrae to reduce wear and tear and other degradation at the locations directly adjacent to the spinal surgery location.

SUMMARY

According to one aspect, a medical apparatus includes a first lateral support member and a second lateral support member, each lateral support member configured for attachment to a first vertebra, and a transverse connection member having a first end, a second end, and an intermediate portion therebetween, the first end configured for coupling to the first lateral support member and the second end configured for coupling to the second lateral support member, and a first extension member having a first end and a second end, the first end configured for coupling to the intermediate portion of the transverse connection member, and the second end configured for coupling to a second vertebra adjacent to the first vertebra.

According to another aspect, a medical apparatus for use proximate a surgery location on a spine of a subject includes a first lateral support member and a second lateral support member, each lateral support member configured for coupling to a portion of the spine proximate a first vertebra. A transverse connection member has a first end, a second end, and an intermediate portion therebetween, with the first end configured for coupling to the first lateral support member and the second end configured for coupling to the second lateral support member. A first extension member has a first end and a second end, with the first end configured for coupling to the intermediate portion of the transverse connection member, and the second end configured for coupling to a spinous process of a second vertebra. A second extension member has a first end and a second end, the second end configured for coupling to a spinous process of a third vertebra.

According to yet another aspect, a method of implanting a medical apparatus proximate a spinal surgery location of a subject includes the steps of implanting a first lateral support member and a second lateral support member proximate the spinal surgery location, and implanting a transverse connection member having a first end, a second end, and an intermediate portion therebetween, and coupling the first end to the first lateral support member and the second end to the second lateral support member, and implanting a first extension member having a first end and a second end, and coupling the first end to the intermediate portion of the transverse connection member, and coupling the second end to a spinous process of a second vertebra.

Alternative exemplary embodiments relate to other features and combinations of features as may be generally recited in the claims.

BRIEF DESCRIPTION OF THE DRAWINGS

The disclosure will become more fully understood from the following detailed description, taken in conjunction with the accompanying figures, wherein like reference numerals refer to like elements, in which.

DETAILED DESCRIPTION

Referring to the FIGURES, a universal medical apparatus and method for use with any of a variety of spinal surgery techniques, such as spinal fusion, laminotomy, laminectomy and diskectomy, etc. are shown according to various exemplary embodiments for transferring loads (e.g. flexing/bending loads, stresses, etc.) and other related stresses from the locations at or directly adjacent to the surgery location (e.g. fused vertebrae, etc.) to other vertebrae above and/or below the surgery location, so that bending loads and other stresses may be spread over (and at least partially accommodated by) such other vertebrae to reduce wear and tear and other degradation at the locations directly adjacent to the surgery location. The medical apparatus and method is intended to provide a medical method and apparatus that can be surgically implanted in a subject (e.g. patient) at one level, or more than one level, in the cervical, thoracic and lumbar regions of the spine. The medical apparatus may be implanted at the time of the underlying surgical procedure, or may also be implanted in subjects having had prior spinal surgery procedures (in the manner of a 'retrofit' or the like) to arrest, minimize or even prevent further degradation to spinal elements adjacent to the surgery location due to reduced mobility or flexibility at the surgery location.

According to the various exemplary embodiments, the medical apparatus and method includes one or more elongated lateral support members (e.g. beams—unilateral, bilateral, etc.) extending substantially parallel (or slightly angled relative to) to the longitudinal axis of the spine and each having end regions (e.g. a first end and a second end) coupled to vertebrae (e.g. at a location proximate the facet joint) proximate the surgery location to provide a stable base (e.g. anchor, foundation, etc.) for the medical apparatus. An elongated transverse connector (e.g. transverse connection member, joist, etc.) has opposite ends (e.g. a first end and a second end) and extends substantially perpendicular to, and is interconnected between and thus supported at any one of a plurality of positions by, the bilateral support members at a location substantially adjacent to the surgery location. An extension member (e.g. strut, bridge, etc.) has a first end coupled to and supported by the transverse connector at any one of a plurality of positions along the transverse connector, and a second end that is coupled to an adjacent vertebrae (e.g. at the spinous process, etc.) above (and/or) below the surgical location, to provide a 'bridge' between the surgery location and one or more adjacent vertebra. The extension member is thus intended to at least partially transfer motion and structural loading applied to the spine at the surgical site to one or more adjacent vertebrae (in a rigid or semi-flexible manner), in order to minimize wear and tear, stress, and other related degradation of spinal elements at or directly adjacent to the surgery location. The extension member (and/or other components of the medical apparatus) may also include dynamic or elastomeric properties, which may (by way of example) provide a progressively increasing transfer of force from one vertebra to another as flexion between the vertebrae increases, and a similarly decreasing transfer of force from one vertebra to another as the degree of flexion between the vertebrae decreases. Such dynamic or elastomeric properties may be provided by any suitable material having resiliently deformable properties or characteristics, such as a metallic or non-metallic material (e.g. which provides a desired spring constant over a desired range of motion, etc.) or any suitable elastomeric material (e.g. having a desired resiliency and memory for extending to a flexed position and returning to an original position, etc.).

According to the illustrated and exemplary embodiments, the medical apparatus and method is intended to bridge the vertebra adjacent to the surgery location to more evenly distribute motion, loads and stresses from the surgery location across one or more adjacent vertebrae (e.g. in a 'load-sharing' or 'load-distributing' manner or the like). The medical apparatus: may be implanted at one or more surgical locations along the spine, may be unilateral or bilateral, may be used in conjunction with any type of spinal surgical technique that results in reduced or otherwise limited mobility or structural capability at the surgery location, may transfer motion and loading to one or more vertebrae both above and below the surgery location, may use structural components that are rigid, flexible, or a combination of rigid-flexible, or may be progressively more rigid or progressively more flexible with increasing motion (e.g. flexion, etc.) by the spine, and may couple to the vertebral elements of a patient using any of a variety of attachment technologies. The dimensions and materials used to form the lateral support members, transverse connector and extension members may vary. In one aspect, any one or more of these components of the medical apparatus and method may comprise a biologically compatible material selected from the group consisting of titanium, a titanium alloy, stainless steel, plastic, a polymer, or any combination thereof.

The transverse connector may have any suitable cross-sectional shape (e.g. substantially flat, or substantially circular, etc.) that is intended to provide the desired structural properties and is suitable for adaptation with and implantation in a human body. The transverse connector and the extension member(s) may be engineered as substantially rigid members with substantially no (or minimal) bending or flexure under the anticipated structural loading conditions upon implantation at the specific spinal location in the body, in order to transfer substantially all (or most) of the loading and movement from the surgery location proximate the first vertebra to the adjacent second vertebra. According to other embodiments, the transverse connector and/or the extension member(s) may be engineered as a semi-rigid (e.g. partially flexible) member with a predetermined bending or flexure under the anticipated structural loading conditions upon implantation at the specific spinal location in the body, in order to transfer a predetermined amount of the loading and movement from the surgery location proximate the first vertebra to the adjacent second vertebra. The degree of rigidity and/or flexibility and/or elasticity of the transverse connector and/or extension member(s) may be adjusted depending upon whether the extension member(s) are arranged in a unilateral or bilateral configuration, and whether the loading and motion are being transferred to vertebra that are above and/or below the surgery location.

According to other embodiments, the medical apparatus and method may include additional extension member(s) for transferring loading and motion from the surgery location to multiple supporting vertebrae above and/or below the surgery location. Such additional extension members may extend directly between the transverse connector at the surgery location and each of such multiple supporting vertebra (e.g. to provide an independent support relationship with each of such vertebra), or such additional extension members may be individually linked between each of the multiple supporting vertebra (e.g. by one spinous process to the next, in an articulated manner that connects such supporting vertebra to one another).

The exact dimensions of the components of the medical apparatus and method may vary, depending upon considerations such as minimizing interference with elements of the spinal column, providing a stable surface upon which to support, or place over, vertebral components, and evenly distributing the load between the vertebral components and the medical apparatus. The lateral support members and the extension member(s) may be attached to the elements of the spinal column in a variety of ways, including, but not limited to screws, pins, welds, clips, snaps and the like. The lateral support members may also comprise a connector for attaching the support to the body, including, but not limited to screws, pins, clips, snaps and the like.

Each of the components of the medical apparatus and method may comprise a variety of materials or combinations of materials. In some embodiments, the components, such as the lateral support members, transverse connector, extension member(s) and connectors, comprise a biologically compatible material. A variety of biologically compatible materials may be used, including, but not limited to metals, such as titanium, titanium alloys, chrome cobalt or stainless steel. Other biocompatible materials include graphite and ceramics, such as hydroxyapatites. Plastics may also be employed. Suitable plastics include polyethylene (e.g. ultrahigh molecular weight polyethylene), polypropylene, polyether ester ketone, and silicones.

The components of the medical apparatus and method may be secured to the spine in a variety of ways. For example, any of the components of the system, including the lateral support members and the extension member(s) comprise a connector for securing the apparatus to the spine. A variety of connectors may be used, including but not limited to screws, hooks or pins. Suitable screws and hooks include, but are not limited to, pedicle screws, polyaxial pedicle screws, lateral mass screws or polyaxial hooks and the like, such as those disclosed in U.S. Pat. Nos. 5,591,166; 5,628,740; 6,626,908; and in U.S. Patent Publication No. 2005/0113927. The connectors may attach to a variety of vertebral elements, including, but not limited to, pedicles, lamina or spinous processes. The system may also include wires or bands in order to tie or hold the components in place.

Further, when implanted, the exact placement of the medical apparatus relative to the spine may vary. Generally, the medical apparatus is positioned at posterior location. In some embodiments, the lateral support members are positioned along the longitudinal axis of the spine. In other embodiments, the lateral support members may be angled relative to the longitudinal axis of the spine. In such embodiments, the lateral support members are positioned to either side of the spinous processes that run along the axis of the spine. The longitudinal axis of the lateral support members are generally aligned with the longitudinal axis of the spine, although non-parallel alignments are within the scope of the invention.

Accordingly, all such variations of the medical apparatus and method are intended to be within the scope of this disclosure.

Figure 1:
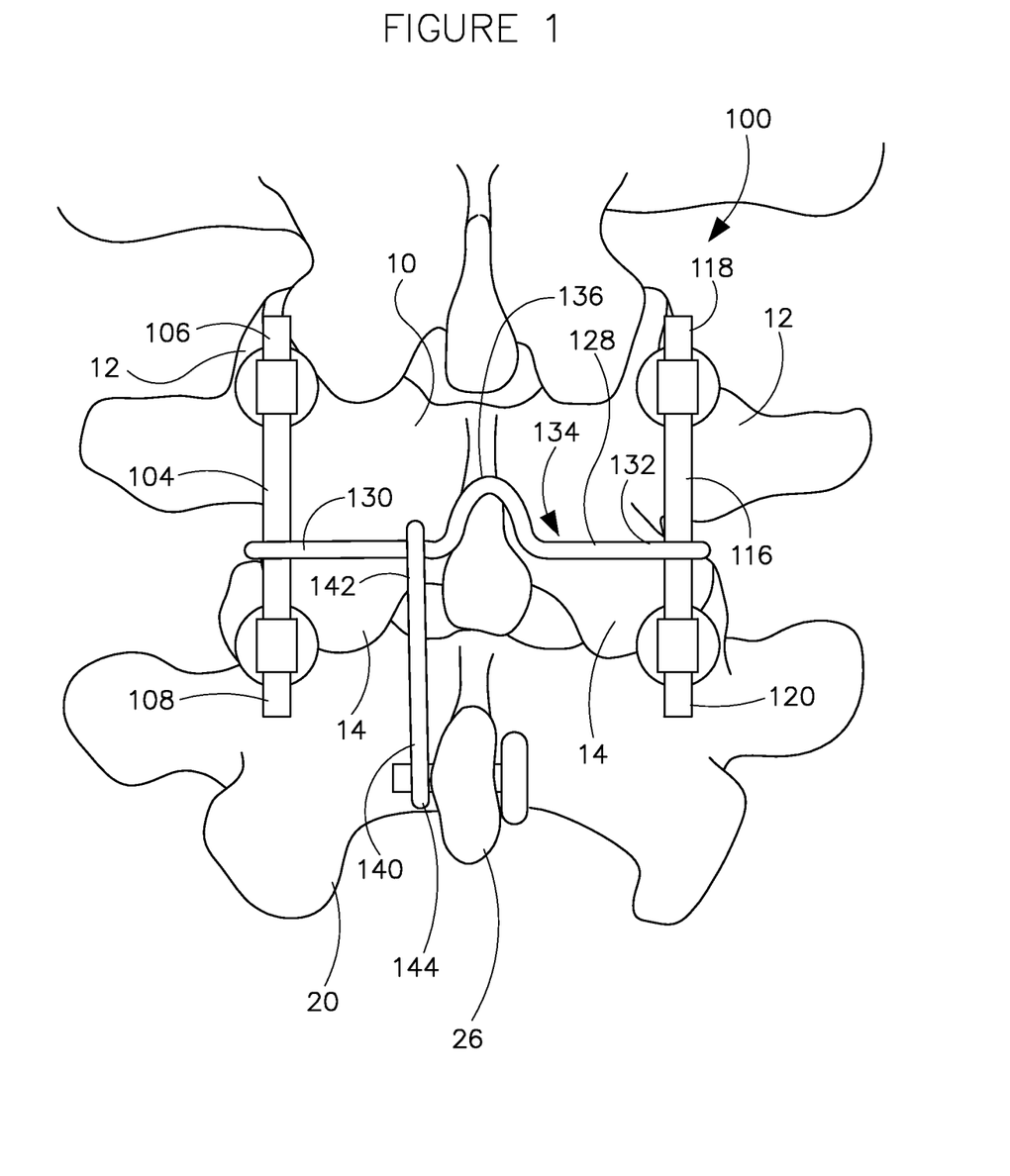
FIG. 1 is a schematic representation of a posterior elevation view of a medical apparatus and method for spinal surgery according to one embodiment.

Referring more particularly now to FIG. 1, a medical apparatus 100 is shown according to one embodiment. Medical apparatus 100 is shown by way of example to include first and second lateral support members 104,116 (providing a bilateral support system), a transverse connector (shown as transverse connection member 128), and an extension member 140. Lateral support members 104,116 are shown as elongated members (e.g. rods, bars, etc.) that each have a first end 106,118 coupled to an upper portion 12 (e.g. facet, etc.) of a first vertebra 10 (corresponding generally to a surgery location), and a second end 108,120 coupled to a lower portion 14 (e.g. facet, etc.) of the first vertebra 10. Transverse connection member 128 is shown having opposite ends 130,132 coupled to and supported by the lateral support members 104,116 at any desired location along the length of the lateral support members. According to the illustrated embodiment, transverse connection member 128 has an intermediate portion 134 with a ridge 136 (or other suitable shape) intended to closely follow the contour (i.e. accommodate) the spinous process 16 of the first vertebra 10. The extension member 140 is shown as a single (unilateral) extension member having a first end 142 coupled to the transverse connection member 128 adjacent to the ridge 136, and a second end 144 that is coupled to the spinous process 26 of a second vertebra 20 (shown for example as below the first vertebra) to provide a rigid or semi-rigid/flexible structural bridge between the first vertebra 10 and the second vertebra 20. The second end 144 of the extension member 140 may be coupled to the spinous process 26 using any suitable technique, such as (but not limited to) a surgical screw and nut, a surgical pin, a surgical claw device, or other suitable bone attachment device.

Figure 2:
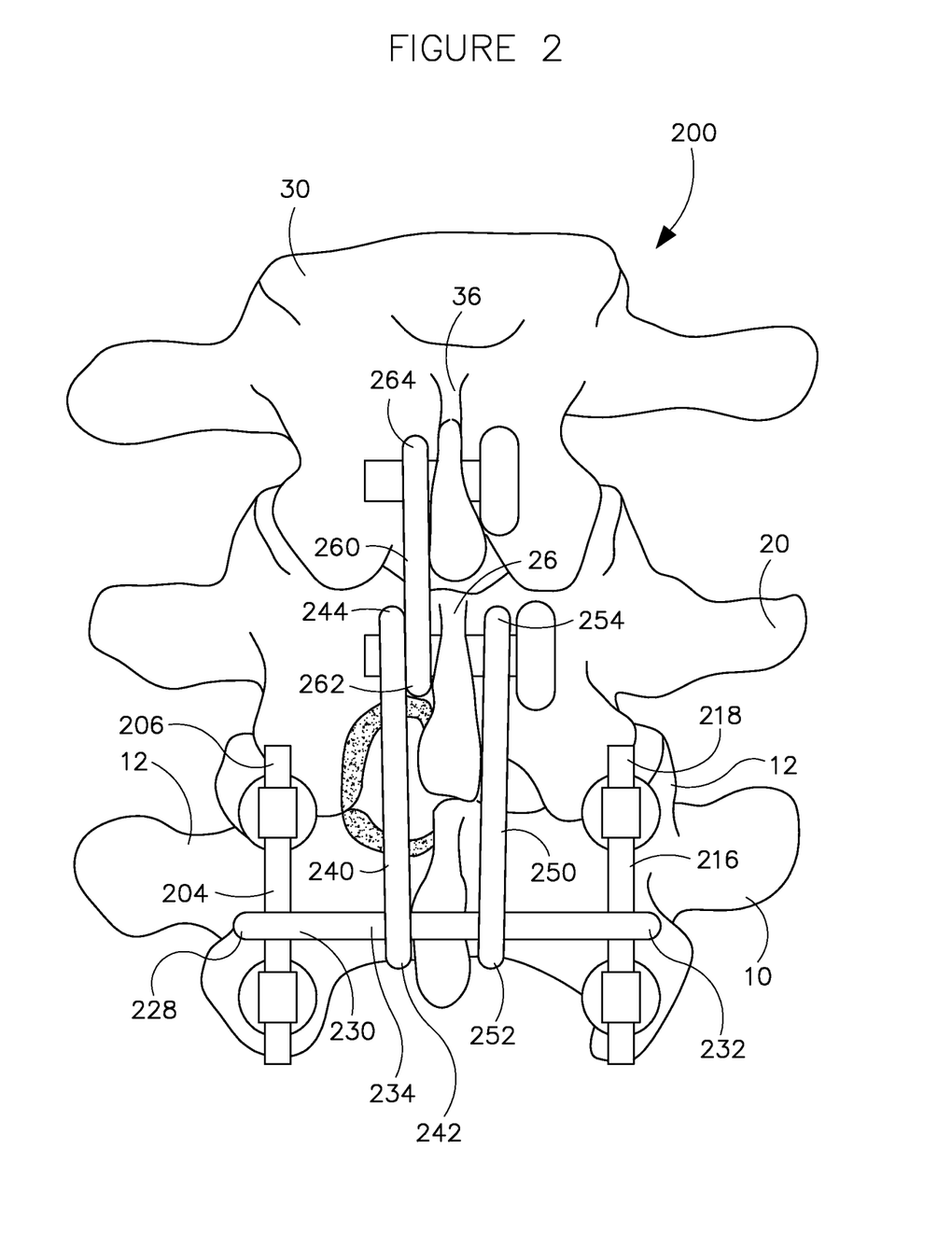
FIG. 2 is a schematic representation of a posterior elevation view of a medical apparatus and method for spinal surgery according to another embodiment.

Referring more particularly now to FIG. 2, a medical apparatus 200 is shown according to another embodiment. Medical apparatus 200 is shown by way of example to be adapted for use with a spinal laminotomy procedure and includes first and second lateral support members 204, 216 (providing a bilateral support system), a transverse connection member 228, and multiple extension members 240, 250, 260. Lateral support members 204, 216 are shown as elongated members (e.g. rods, bars, etc.) that each have a first end 206, 218 coupled to an upper portion 12 of a first vertebra 10 (corresponding generally to a spinal surgery location), and a second end 208,220 coupled to a lower portion 14 of the first vertebra 10. Transverse connection member 228 is shown having opposite ends 230, 232 coupled to and supported by the lateral support members 204, 216. According to the illustrated embodiment, transverse connection member 228 is a substantially linear member (i.e. without a ridge such as that shown in FIG. 1) due to removal of the spinous process of the first vertebra as part of the laminotomy procedure. Extension members 240, 250 are shown as a double (bilateral) extension arrangement, each having a first end 242, 252 coupled to the intermediate portion 234 of the transverse connection member 228, and a second end 244, 254 that is coupled to the spinous process 26 of a second vertebra 20 (shown above the first vertebra 10) to provide a rigid, or semi-rigid/flexible structural bridge between the first vertebra 10 and the second vertebra 20. The third extension member 260 is shown coupled between the spinous process 26 of the second vertebra 20 and the spinous process 36 of a third vertebra 30 to provide a rigid, or semi-rigid/flexible structural bridge between the second vertebra 20 and the third vertebra 30.

Figure 3:
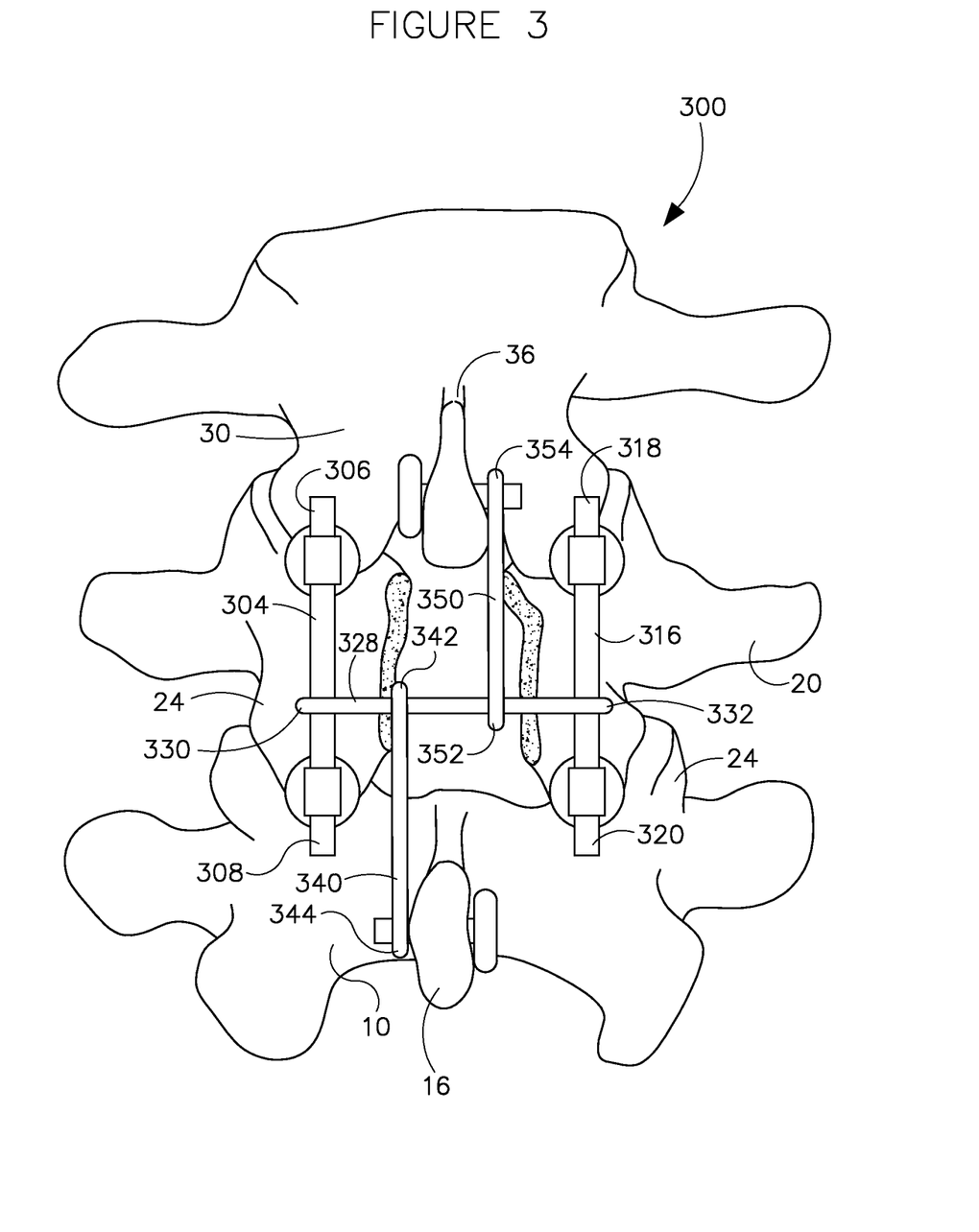
FIG. 3 is a schematic representation of a posterior elevation view of a medical apparatus and method for spinal surgery according to yet another embodiment.

Referring more particularly now to FIG. 3, a medical apparatus 300 is shown according to yet another embodiment. Medical apparatus 300 is shown by way of example to be adapted for use with a spinal laminectomy procedure and includes first and second lateral support members 304, 316 (providing a bilateral support system), a transverse connection member 328, and multiple extension members 340, 350. Lateral support members 304, 316 are shown as elongated members (e.g. rods, bars, etc.) that each have a first end 306, 318 coupled to an upper portion (e.g. facet, etc.) 22 of a second vertebra 20, and a second end 308, 320 coupled to a lower portion 24 (e.g. facet, etc.) of the second vertebra 20 (proximate a spinal surgery location). Transverse connection member 328 is shown having opposite ends 330, 332 coupled to and supported by the lateral support members 304, 316. According to the illustrated embodiment, transverse connection member 328 is a substantially linear member (i.e. without a ridge such as that shown in FIG. 1) due to removal of the spinal process of the second vertebra as part of the laminectomy procedure. Extension members 340, 350 are shown as two unilateral extensions each having a first end 342, 352 coupled to the transverse connection member 328. Extension member 340 has a second end 344 that is coupled to the spinous process 16 of a (lower) first vertebra 10 (below the second vertebra) to provide a rigid, or semi-rigid/flexible and/or dynamic/elastic structural bridge between the lower first vertebra 10 and the second vertebra 20. The second extension member 350 has a first end 352 coupled to the transverse connection member 328 and second end 354 coupled to the spinous process 36 of an (upper) third vertebra 30 (above the second vertebra) to provide a rigid, or semi-rigid/flexible and/or dynamic/elastic structural bridge between the second vertebra 20 and the upper third vertebra 30.

Figure 4:
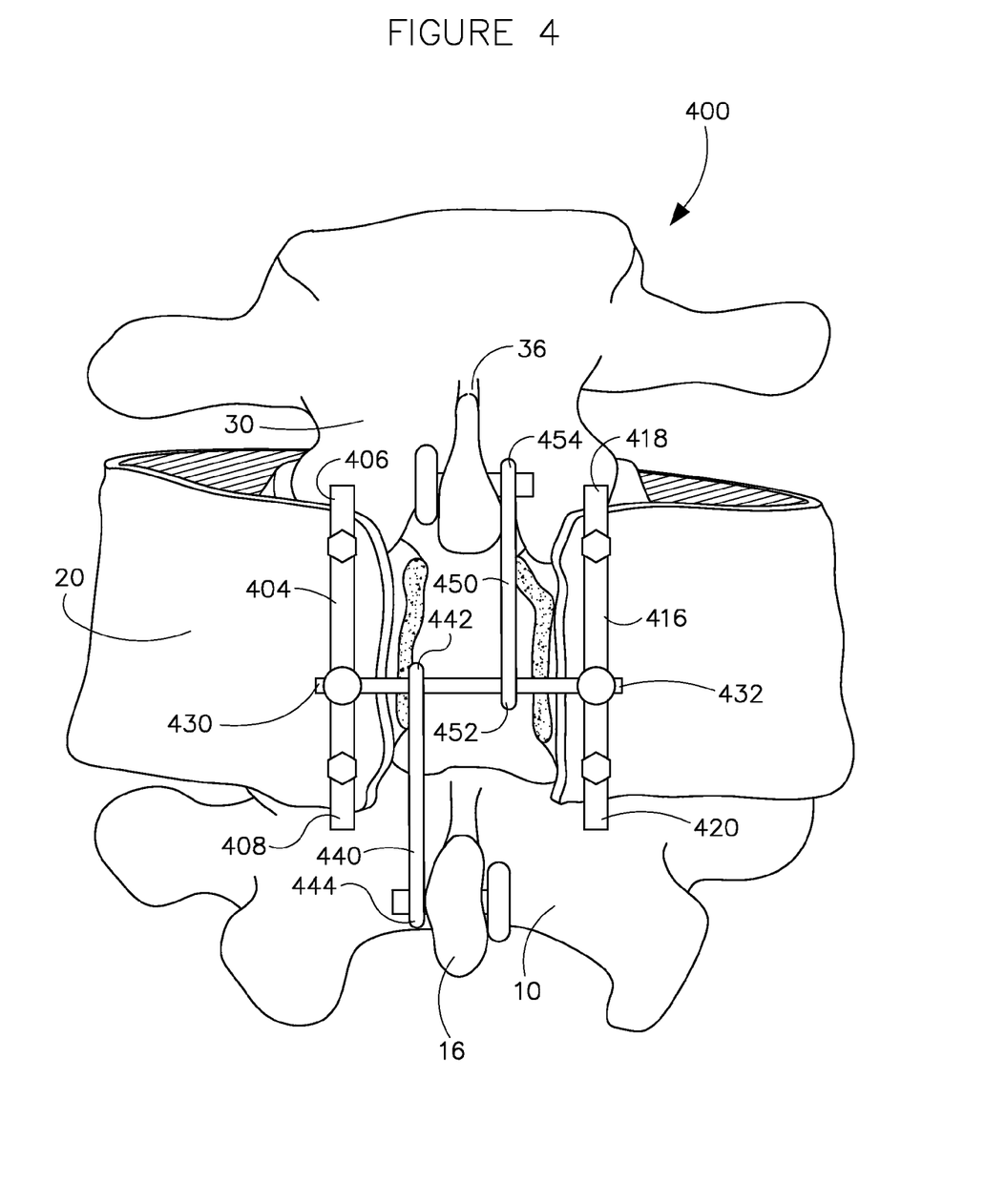
FIG. 4 is a schematic representation of a posterior elevation view of a medical apparatus and method for spinal surgery according to still another embodiment.

Referring more particularly now to FIG. 4, a medical apparatus 400 is shown according to yet another embodiment. Medical apparatus 400 is shown by way of example to be adapted for use with a spinal fusion procedure and includes first and second lateral support members 404, 416 (such as metallic supports that may be integral to the fusion material proximate a second vertebra 20 and thus providing a bilateral support system), a transverse connection member 428, and multiple extension members 440, 450. Transverse connection member 428 is shown having opposite ends 430, 432 coupled to and supported by the lateral support members 404, 416. Extension members 440, 450 are shown as two unilateral extensions, each having a first end 442, 452 coupled to the transverse connection member 428. Extension member 440 has a second end 444 that is coupled to the spinous process 16 of a (lower) first vertebra 10 (below the second vertebra) to provide a rigid, or semi-rigid/flexible and/or dynamic/elastic structural bridge between the lower first vertebra 10 and the second vertebra 20. The extension member 450 has a first end 452 coupled between the transverse connection member 428 and a second end 454 coupled to the spinous process 36 of an (upper) third vertebra 30 (above the second vertebra) to provide a rigid, or semi-rigid/flexible dynamic/elastic structural bridge between the second vertebra 20 and the upper third vertebra 30.

Figure 5A:
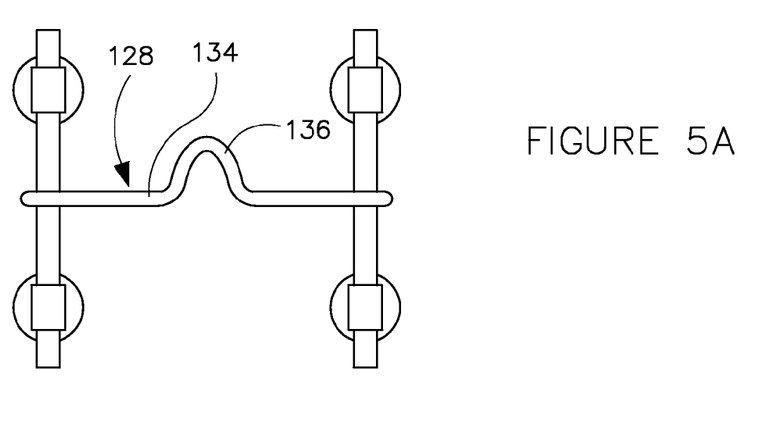
FIGS. 5A-5C are schematic representations of an elevation view of a transverse connector for a medical apparatus and method for spinal surgery according to exemplary embodiments.
Figure 5B:
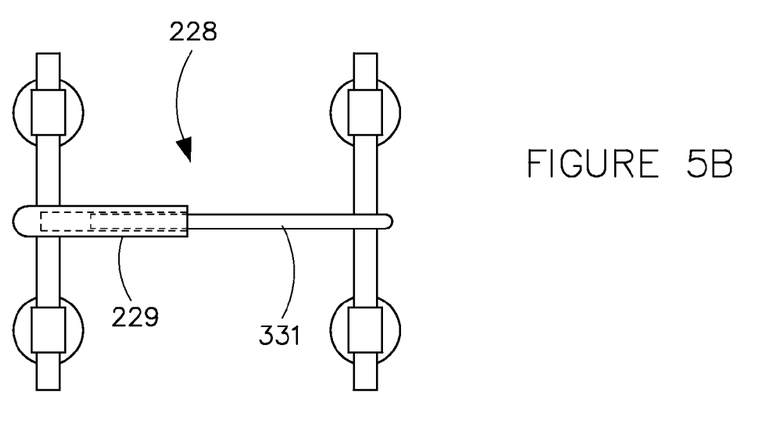
Figure 5C:
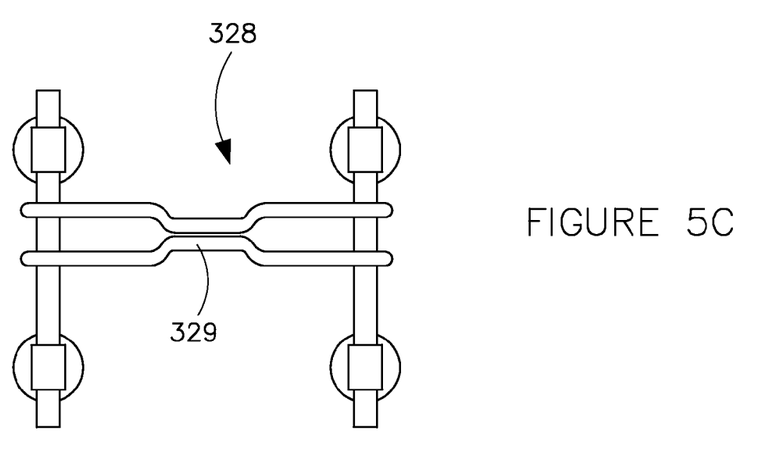

Referring more particularly now to FIGS. 5A-5C, the transverse connection member is shown according to several embodiments. According to one embodiment as shown by way of example in FIGS. 1 and 5A, the transverse connection member 128 may include an intermediate portion 134 with a ridge 136 or other suitable shape or contour intended to accommodate existing bone structure (e.g. spinal process, etc.) of a vertebra remaining after the primary surgical procedure is completed. According to another embodiment shown in FIG. 5B, the transverse connection member 228 may be provided with an adjustment feature, shown by way of example as two portions 229, 231 that are telescopingly engagable with one another, to accommodate variable spacing between the lateral support members. According to the embodiment of FIG. 5C, the transverse connection member 328 may include a cross section having variable width, thickness of other variable dimensions to accommodate placement and positioning of the device in a subject. Further, the transverse connection member 328 may have a neck portion 329 intended to help retain the first end of an extension member attached thereto. The transverse connection member may also be configured to flex or bend a certain amount to provide a desired degree of elasticity in the connection between adjacent spinous processes. According to other alternative embodiments, the transverse connection member may have other sizes, shapes and configurations for coupling the extension members to a support such as the lateral support members. According to other embodiments, the transverse connection members and the extension member(s) may be provided as a single integrated component.

In yet another aspect, methods of using the medical apparatus for spinal surgery and components thereof are provided. The methods comprise implanting into a subject any of the medical components disclosed herein. The apparatuses may be implanted by an open procedure, endoscopically or laprascopically. In some embodiments, the methods further comprise contacting the lateral support members with at least a portion of the lamina or facet of a single vertebra or multiple adjacent vertebrae, coupling a transverse connector between the lateral support members and coupling a flexion extension member between the transverse connector and the spinous process of one or more adjacent vertebra. In other embodiments, the methods further comprise attaching the components to the spine via a connector as described above. The implantation of the components may take place in stages and in various sequences.

Figure 6:
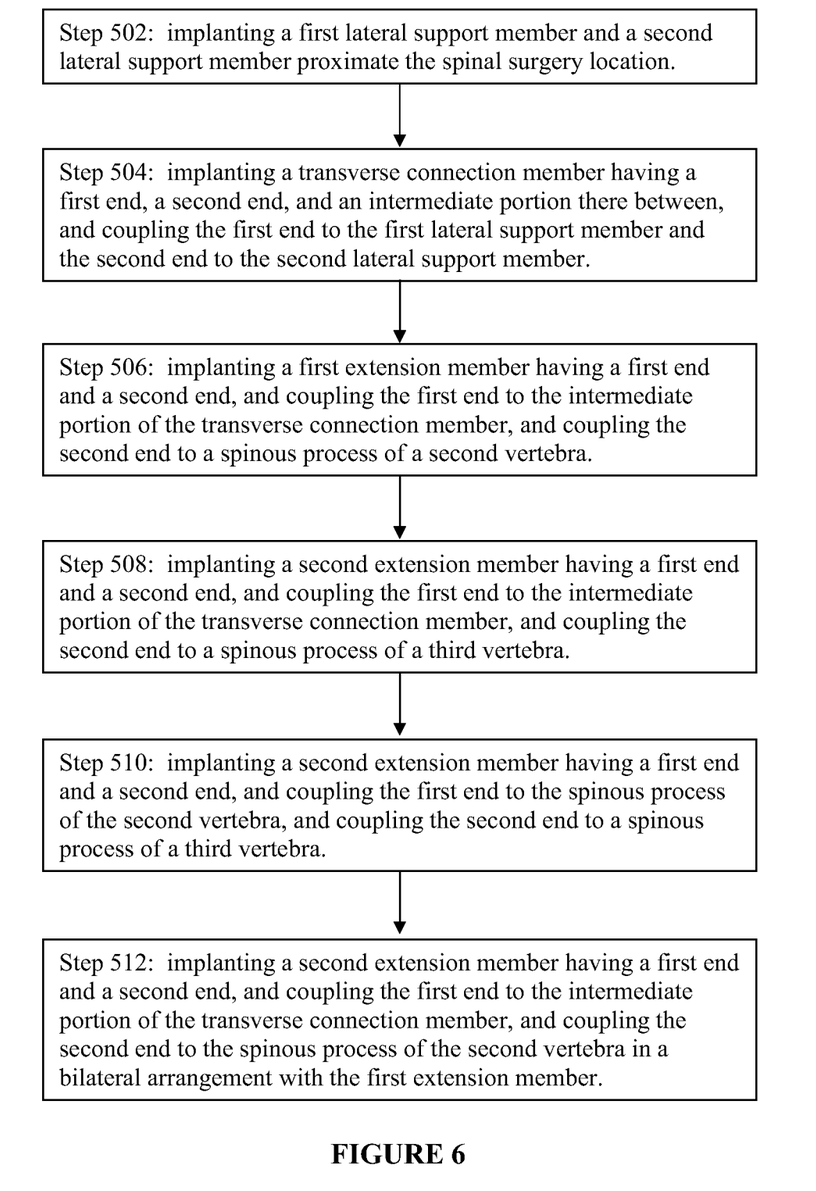
FIG. 6 is a flow diagram of a method of implanting a medical apparatus for spinal surgery according to an exemplary embodiment.

Referring more particularly to FIG. 6, a method 500 of implanting a medical apparatus proximate a spinal surgery location in a subject is outlined according to an exemplary embodiment to include the following steps, which may be performed in an order other than the order which follows, and in which certain steps may be varied or omitted. Step 502: implanting a first lateral support member and a second lateral support member proximate the spinal surgery location. Step 504: implanting a transverse connection member having a first end, a second end, and an intermediate portion therebetween, and coupling the first end to the first lateral support member and the second end to the second lateral support member. Step 506: implanting a first extension member having a first end and a second end, and coupling the first end to the intermediate portion of the transverse connection member, and coupling the second end to a spinous process of a second vertebra. Step 508: implanting a second extension member having a first end and a second end, and coupling the first end to the intermediate portion of the transverse connection member, and coupling the second end to a spinous process of a third vertebra. Step 510: implanting a second extension member having a first end and a second end, and coupling the first end to the spinous process of the second vertebra, and coupling the second end to a spinous process of a third vertebra. Step 512: implanting a second extension member having a first end and a second end, and coupling the first end to the intermediate portion of the transverse connection member, and coupling the second end to the spinous process of the second vertebra in a bilateral arrangement with the first extension member.

According to any exemplary embodiment, a medical apparatus and method for spinal surgery includes one or more lateral support members extending substantially parallel or slightly angled relative to the longitudinal axis of the spine, each being coupled to a vertebra proximate the surgery location to provide a stable base for the system. A transverse connection member extends substantially perpendicular to, and is interconnected between and thus supported by, the lateral support members at a location substantially adjacent to the surgery location. One or more extension members have a first end coupled to and supported by the transverse connection member, and a second end that is coupled to an adjacent vertebra at the spinous process, etc. above and/or below the surgical location, to provide a 'bridge' between the surgery location and the adjacent vertebra.

The figures show examples of a medical apparatus and method for spinal surgery according various embodiments. The embodiments shown in the figures are intended only to exemplify the invention and should not be construed to limit the invention to any particular embodiment. The drawings are not necessarily to scale and the relative dimensions of the components of the system provided therein may deviate from those shown in the figures.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

For the purposes of this disclosure and unless otherwise specified, "a" or "an" means "one or more." All patents, applications, references and publications cited herein are incorporated by reference in their entirety to the same extent as if they were individually incorporated by reference.

As utilized herein, the terms "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It should be noted that the orientation of various elements may differ according to other exemplary embodiments, and that such variations are intended to be encompassed by the present disclosure.

It is also important to note that the construction and arrangement of the medical apparatus and method and components thereof as shown in the various exemplary embodiments is illustrative only. Although only a few embodiments of the present inventions have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, orientations, etc.) without materially departing from the novel teachings and advantages of the subject matter disclosed herein. For example, elements shown as integrally formed may be constructed of multiple parts or elements, the position of elements may be reversed or otherwise varied, and the nature or number of discrete elements or positions may be altered or varied. Accordingly, all such modifications are intended to be included within the scope of the present invention as defined in the appended claims. The order or sequence of any process or method steps may be varied or re-sequenced according to alternative embodiments. Other substitutions, modifications, changes and omissions may be made in the design, operating conditions and arrangement of the various exemplary embodiments without departing from the scope of the present inventions.

What is claimed is:

1. A medical apparatus, comprising:
    a first lateral support member and a second lateral support member, each lateral support member having a first end and a second end, with the first end and the second end configured for attachment to a first vertebra;
    a transverse connection member having a first end, a second end, and an intermediate portion therebetween, the first end configured for coupling to the first lateral support member and the second end configured for coupling to the second lateral support member;

a connector configured for coupling to the spinous process of a second vertebra adjacent to the first vertebra and configured to extend from the spinous process of the second vertebra in a direction substantially parallel to the transverse connection member;

a first extension member having a first end and a second end, the first end pivotally coupled to the intermediate portion of the transverse connection member, and the second end pivotally coupled to the connector to provide pivotable movement of the first extension member about both a first axis defined by the transverse connection member and a second axis defined by the connector, wherein the first axis and the second axis are substantially parallel to one another and substantially parallel to both the transverse connection member and the direction that the connector extends from the second vertebra during use; and a second extension member having a first end and a second end, the first end configured for coupling to the intermediate portion of the transverse connection member, and the second end configured for coupling to a third vertebra, wherein the third vertebra is adjacent the first vertebra and opposite the second vertebra;

wherein the intermediate portion of the transverse connection member has substantially flat outer surfaces and is formed from an elastomeric material having a memory that is resiliently deformable to extend to a flexed position under a predetermined loading condition and to return to an original position to provide, along with the first extension member, an elastic structural bridge between the first vertebra and the second vertebra.

2. The medical apparatus of claim 1 wherein the first end of the first extension member is configured for coupling at any one of a plurality of locations along a length of the intermediate portion of the transverse connection member.

3. The medical apparatus of claim 1, wherein the first and second lateral support members extend substantially parallel to one another and are configured to extend along a longitudinal axis of a spine of a subject.

4. The medical apparatus of claim 1, wherein the connector comprises a pin joint configured to be pivotally movable about the spinous process of the second vertebra.

5. The medical apparatus of claim 1, wherein the first and second support members each comprise a first end and a second end, the first ends and the second ends configured for attachment to the first vertebra.

6. The medical apparatus of claim 1, wherein the intermediate portion of the transverse connection member comprises a ridge portion configured to accommodate a spinous process of the first vertebra.

7. The medical apparatus of claim 1, wherein the transverse connection member comprises a length adjustment feature.

8. The medical apparatus of claim 7, wherein the length adjustment feature comprises a first portion and a second portion that are telescopingly engagable with each other.

9. The medical apparatus of claim 1, wherein the intermediate portion further comprises a neck region.

10. The medical apparatus of claim 1, wherein the transverse connection member and the first extension member are both resiliently deformable and have a spring constant that provides a progressively increasing transfer of force from the first vertebra to the second vertebra as flexion between the vertebrae increases, and a decreasing transfer of force from the first vertebra to the second vertebra as the degree of flexion between the vertebrae decreases.

11. A medical apparatus for use proximate a surgery location on a spine of a subject, comprising:

a first elongated lateral support member and a second elongated lateral support member, each lateral support member having a first end and a second end with a length therebetween, the first end and the second end configured for coupling to a portion of the spine proximate a first vertebra;

a transverse connection member having a first end, a second end, and an intermediate portion therebetween, the first end configured for coupling at a predetermined location along the length of the first lateral support member and the second end configured for coupling at a predetermined location along the length of the second lateral support member;

a first connector configured for coupling to the spinous process of a second vertebra adjacent to the first vertebra and configured to extend from the spinous process of the second vertebra in a direction substantially parallel to the transverse connection member;

a first extension member having a first end and a second end, the first end pivotally coupled to the intermediate portion of the transverse connection member, and the second end pivotally coupled to the first connector to provide pivotable movement of the first extension member about both a first axis defined by the transverse connection member and a second axis defined by the first connector;

a second connector configured for coupling to the spinous process of a third vertebra adjacent to the first vertebra opposite the second vertebra and configured to extend from the spinous process of the third vertebra in a direction substantially parallel to the transverse connection member; and a second extension member having a first end and a second end, the first end pivotally coupled to the intermediate portion of the transverse connection member, the second end pivotally coupled to the second connector to provide pivotable movement about both the first axis and a third axis defined by the second connector;

wherein the first axis, the second axis and the third axis are substantially parallel to one another and substantially parallel to both the transverse connection member and the directions that the first connector and the second connector extend from the second and third vertebrae during use.

12. The medical apparatus of claim 11, wherein the first end of the second extension member is configured for coupling to the transverse connection member at any one of a plurality of locations along the length of the intermediate portion.

* * * * *